United States Patent
Sarager et al.

(10) Patent No.: US 8,704,011 B2
(45) Date of Patent: Apr. 22, 2014

(54) SEPARATING ETHANOL AND ETHYL ACETATE UNDER LOW PRESSURE CONDITIONS

(75) Inventors: Lincoln Sarager, Houston, TX (US); R. Jay Warner, Houston, TX (US); Trinity Horton, Houston, TX (US); David Lee, Seabrook, TX (US); Victor J. Johnston, Houston, TX (US); Manuel Salado, Seabrook, TX (US)

(73) Assignee: Celanese International Corporation, Dallas, TX (US)

( * ) Notice: Subject to any disclaimer, the term of this patent is extended or adjusted under 35 U.S.C. 154(b) by 204 days.

(21) Appl. No.: 13/094,688

(22) Filed: Apr. 26, 2011

(65) Prior Publication Data

US 2012/0010440 A1   Jan. 12, 2012

Related U.S. Application Data

(60) Provisional application No. 61/332,696, filed on May 7, 2010.

(51) Int. Cl.
*C07C 27/04* (2006.01)

(52) U.S. Cl.
USPC .......................... 568/885; 568/880; 568/881

(58) Field of Classification Search
None
See application file for complete search history.

(56) References Cited

U.S. PATENT DOCUMENTS

| | | |
|---|---|---|
| 2,649,407 A | 8/1953 | Harrison |
| 2,702,783 A | 2/1955 | Harrison |
| 2,882,244 A | 4/1959 | Milton |
| 3,130,007 A | 4/1964 | Breck |
| 3,408,267 A | 10/1968 | Miller |
| 3,445,345 A | 5/1969 | Adam |
| 3,478,112 A | 11/1969 | Adam |
| 3,990,952 A | 11/1976 | Katzen |
| 4,275,228 A | 6/1981 | Gruffaz |
| 4,306,942 A | 12/1981 | Brush |
| 4,317,918 A | 3/1982 | Takano |
| 4,319,058 A | 3/1982 | Kulprathipanja |
| 4,379,028 A | 4/1983 | Berg |
| 4,395,576 A | 7/1983 | Kwantes |
| 4,398,039 A | 8/1983 | Pesa |
| 4,421,939 A | 12/1983 | Kiff |
| 4,422,903 A | 12/1983 | Messick |
| 4,454,358 A | 6/1984 | Kummer |
| 4,465,854 A | 8/1984 | Pond |
| 4,471,136 A | 9/1984 | Larkins |
| 4,480,115 A | 10/1984 | McGinnis |
| 4,492,808 A | 1/1985 | Hagen |
| 4,497,967 A | 2/1985 | Wan |
| 4,520,213 A | 5/1985 | Victor |
| 4,541,897 A | 9/1985 | Sommer |
| 4,626,321 A | 12/1986 | Grethlein |
| 4,678,543 A | 7/1987 | Houben |
| 4,692,218 A | 9/1987 | Houben |
| 4,777,303 A | 10/1988 | Kitson |
| 4,804,791 A | 2/1989 | Kitson |
| 4,842,693 A | 6/1989 | Wheldon |
| 4,961,826 A | 10/1990 | Grethlein |
| 4,985,572 A | 1/1991 | Kitson |
| 4,990,655 A | 2/1991 | Kitson |
| 4,994,608 A | 2/1991 | Torrence |
| 5,001,259 A | 3/1991 | Smith |
| 5,026,908 A | 6/1991 | Smith |
| 5,035,776 A | 7/1991 | Knapp |
| 5,061,671 A | 10/1991 | Kitson |
| 5,124,004 A | 6/1992 | Grethlein |
| 5,144,068 A | 9/1992 | Smith |
| 5,149,680 A | 9/1992 | Kitson |
| 5,185,481 A | 2/1993 | Muto |
| 5,215,902 A | 6/1993 | Tedder |
| 5,227,141 A | 7/1993 | Kim |
| 5,233,099 A | 8/1993 | Tabata |
| 5,237,108 A | 8/1993 | Marraccini |
| 5,250,271 A | 10/1993 | Horizoe |
| 5,348,625 A | 9/1994 | Berg |
| 5,415,741 A | 5/1995 | Berg |
| 5,437,770 A | 8/1995 | Berg |
| 5,445,716 A | 8/1995 | Berg |
| 5,449,440 A | 9/1995 | Rescalli |
| RE35,377 E | 11/1996 | Steinberg |
| 5,599,976 A | 2/1997 | Scates |
| 5,762,765 A | 6/1998 | Berg |

(Continued)

FOREIGN PATENT DOCUMENTS

| CN | 102091429 | 6/2011 |
|---|---|---|
| EP | 0104197 | 4/1984 |

(Continued)

OTHER PUBLICATIONS

Alcala, et al., (2005). Experimental and DFT studies of the conversion of ethanol and acetic acid on PtSn-based catalysts, Journal of Physical Chemistry, 109(6), 2074-2085.

(Continued)

*Primary Examiner* — Sudhakar Katakam (57) ABSTRACT

A crude ethanol product obtained from the hydrogenation of acetic acid comprises ethanol and ethyl acetate. Using a distillation column operated at a pressure of from 0.1 to 100 kPa, the ethyl acetate and ethanol may be effectively separated. In addition, maintaining the amount of water that is fed to the distillation column to an amount less than 10 wt. %, based on the weight of all components fed to the distillation column, provides an energy benefit.

16 Claims, 3 Drawing Sheets

(56) References Cited

U.S. PATENT DOCUMENTS

| | | | |
|---|---|---|---|
| 5,770,770 A | 6/1998 | Kim | |
| 5,800,681 A | 9/1998 | Berg | |
| 5,821,111 A | 10/1998 | Grady | |
| 5,993,610 A | 11/1999 | Berg | |
| 6,121,498 A | 9/2000 | Tustin | |
| 6,143,930 A | 11/2000 | Singh | |
| 6,232,352 B1 | 5/2001 | Vidalin | |
| 6,294,703 B1 | 9/2001 | Hara | |
| 6,375,807 B1 | 4/2002 | Nieuwoudt | |
| 6,509,180 B1 | 1/2003 | Verser | |
| 6,627,770 B1 | 9/2003 | Cheung | |
| 6,657,078 B2 | 12/2003 | Scates | |
| 6,685,754 B2 | 2/2004 | Kindig | |
| 6,693,213 B1 | 2/2004 | Kolena | |
| 6,723,886 B2 | 4/2004 | Allison | |
| 6,809,217 B1 * | 10/2004 | Colley et al. | 560/231 |
| 6,906,228 B2 | 6/2005 | Fischer | |
| 6,927,048 B2 | 8/2005 | Verser | |
| 7,005,541 B2 | 2/2006 | Cheung | |
| 7,074,603 B2 | 7/2006 | Verser | |
| 7,115,772 B2 | 10/2006 | Picard | |
| 7,208,624 B2 | 4/2007 | Scates | |
| 7,297,236 B1 | 11/2007 | Vander Griend | |
| 7,351,559 B2 | 4/2008 | Verser | |
| 7,399,892 B2 | 7/2008 | Rix | |
| 7,507,562 B2 | 3/2009 | Verser | |
| 7,553,397 B1 | 6/2009 | Colley | |
| 7,572,353 B1 | 8/2009 | Vander Griend | |
| 7,601,865 B2 | 10/2009 | Verser | |
| 7,608,744 B1 | 10/2009 | Johnston | |
| 7,682,812 B2 | 3/2010 | Verser | |
| 7,732,173 B2 | 6/2010 | Mairal | |
| 7,744,727 B2 | 6/2010 | Blum | |
| 7,863,489 B2 | 1/2011 | Johnston | |
| 7,884,253 B2 | 2/2011 | Stites | |
| 7,888,082 B2 | 2/2011 | Verser | |
| 2006/0019360 A1 | 1/2006 | Verser | |
| 2007/0270511 A1 | 11/2007 | Melnichuk | |
| 2008/0135396 A1 | 6/2008 | Blum | |
| 2008/0193989 A1 | 8/2008 | Verser | |
| 2009/0014313 A1 | 1/2009 | Lee | |
| 2009/0023192 A1 | 1/2009 | Verser | |
| 2009/0069609 A1 | 3/2009 | Kharas | |
| 2009/0081749 A1 | 3/2009 | Verser | |
| 2009/0166172 A1 | 7/2009 | Casey | |
| 2009/0281354 A1 | 11/2009 | Mariansky | |
| 2009/0318573 A1 | 12/2009 | Stites | |
| 2010/0029980 A1 | 2/2010 | Johnston | |
| 2010/0029995 A1 | 2/2010 | Johnston | |
| 2010/0030001 A1 | 2/2010 | Chen | |
| 2010/0030002 A1 | 2/2010 | Johnston | |
| 2010/0121114 A1 | 5/2010 | Weiner | |
| 2010/0197485 A1 | 8/2010 | Johnston | |
| 2011/0082322 A1 | 4/2011 | Jevtic | |

FOREIGN PATENT DOCUMENTS

| | | |
|---|---|---|
| EP | 0167300 | 1/1986 |
| EP | 0456647 | 7/1990 |
| EP | 0990638 | 4/2000 |
| EP | 2060553 | 5/2009 |
| EP | 2060553 A1 * | 5/2009 |
| EP | 2060555 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| JP | 4-193304 | 7/1992 |
| WO | 8303409 | 10/1983 |
| WO | 03011809 | 2/2003 |
| WO | 2005044783 | 5/2005 |
| WO | 2008135192 | 11/2008 |
| WO | 2009009322 | 1/2009 |
| WO | 2009009323 | 1/2009 |
| WO | 2009048335 | 4/2009 |
| WO | 2009063176 | 5/2009 |
| WO | 2010055285 | 5/2010 |

OTHER PUBLICATIONS

Amit M. Goda et al., DFT modeling of selective reduction of acetic acid to acetaldehyde on Pt-based bimetallic catalysts, 20th NAM, Houston, TX, Jun. 17-22, 2007 available online at http://www.nacatsoc.org/20nam/abstracts/O-S9-18.pdf.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Hilmen, Separation of Azeotropic Mixtures: Tools for Analysis and Studies on Batch Distillation Operation (Nov. 2000) p. 17-20.

International Search Report and Written Opinion for PCT/US2011/035543 mailed Oct. 12, 2011.

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Rachmady, Acetic Acid Reduction by H2 on Bimetallic Pt Fe Catalysts, Journal of Catalysis 209, 87-98 (Apr. 1, 2002), Elsevier Science (USA).

Santori et al. (2000). Hydrogenation of carbonylic compounds on Pt/SiO2 catalysts modified with SnBu4, Studies in Surface Science and Catalysis, 130, 2063-2068.

ZeaChem, Inc., Technology Overview, Lakewood, Colorado www.zeachem.com, 2008.

Zheng, et al. (2007). Preparation and catalytic properties of a bimetallic Sn-Pt complex in the supercages of NaY zeolite by use of surface organometallic chemistry, Applied Organometallic Chemistry, 21(10), 836-840.

Written Opinion for PCT/US2011/035543 mailed Jun. 22, 2012.

International Preliminary Report on Patentability for PCT/US2011/035543 mailed Aug. 7, 2012.

* cited by examiner

SEPARATING ETHANOL AND ETHYL ACETATE UNDER LOW PRESSURE CONDITIONS

CROSS REFERENCE TO RELATED APPLICATIONS

This application claims priority to U.S. Provisional App. No. 61/332,696, filed on May 7, 2010, the entirety of which is incorporated herein by reference.

FIELD OF THE INVENTION

The present invention relates generally to processes for producing ethanol and, in particular, to separating ethanol and ethyl acetate under low pressure conditions.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are formed with ethanol or are formed in side reactions. These impurities limit the production and recovery of ethanol from such reaction mixtures. For example, during hydrogenation, esters are produced that together with ethanol and/or water form azeotropes, which are difficult to separate. In addition when conversion is incomplete, unreacted acid remains in the crude ethanol product, which must be removed to recover ethanol.

EP02060553 describes a process for converting hydrocarbons to ethanol involving converting the hydrocarbons to ethanoic acid and hydrogenating the ethanoic acid to ethanol. The stream from the hydrogenation reactor is separated to obtain an ethanol stream and a stream of acetic acid and ethyl acetate, which is recycled to the hydrogenation reactor.

The need remains for improved processes for recovering ethanol from a crude product obtained by reducing alkanoic acids, such as acetic acid, and/or other carbonyl group-containing compounds.

SUMMARY OF THE INVENTION

In a first embodiment, the present invention is directed to a process for producing ethanol, comprising hydrogenating acetic acid from an acetic acid feed stream in a reactor to form a crude ethanol product comprising ethanol, ethyl acetate, and acetic acid; separating at least a portion of the crude ethanol product in a first column into a first distillate comprising ethanol and ethyl acetate and a first residue comprising acetic acid; and separating at least a portion of the first distillate in a second column under low pressure conditions into a second distillate comprising ethyl acetate and a second residue comprising ethanol.

In a second embodiment, the present invention is directed to a process for producing ethanol, comprising providing a crude ethanol product comprising ethanol, ethyl acetate, acetic acid, and water; separating at least a portion of the crude ethanol product in a first column into a first distillate comprising ethanol and ethyl acetate and a first residue comprising acetic acid; and separating at least a portion of the first distillate in a second column under low pressure conditions into a second distillate comprising ethyl acetate and a second residue comprising ethanol.

In a third embodiment, the present invention is directed to a process for producing ethanol, comprising hydrogenating acetic acid from an acetic acid feed stream in a reactor to form a crude ethanol product comprising ethanol, ethyl acetate, and acetic acid; separating at least a portion of the crude ethanol product in a first column into a first distillate comprising ethanol and ethyl acetate and a first residue comprising acetic acid; and separating at least a portion of the first distillate in a second column into a second distillate comprising ethyl acetate and a second residue comprising ethanol, wherein a total concentration of water fed to the second column is less than 10 wt. %, based on the total weight of all components fed to the second column.

In a fourth embodiment, the present invention is directed to a process for producing ethanol, comprising hydrogenating acetic acid from an acetic acid feed stream in a reactor to form a crude ethanol product comprising ethanol, ethyl acetate, and water; separating at least a portion of the crude ethanol product in a first column into a first distillate comprising ethanol and ethyl acetate and a first residue comprising water; and separating at least a portion of the first distillate in a second column under low pressure conditions into a second distillate comprising ethyl acetate and a second residue comprising ethanol. The conversion of acetic acid in the reactor may be greater than 90%, and more preferably greater than 99%.

BRIEF DESCRIPTION OF DRAWINGS

The invention is described in detail below with reference to the appended drawings, wherein like numerals designate similar parts.

DETAILED DESCRIPTION OF THE INVENTION

Introduction

The present invention relates to processes for recovering ethanol produced by hydrogenating acetic acid in the presence of a catalyst. The hydrogenation reaction produces a crude ethanol product that comprises ethanol, water, ethyl acetate, unreacted acetic acid, and other impurities. Ethyl acetate is typically co-produced with ethanol and may also be formed by esterification of unreacted acetic acid. To improve operating efficiencies, the processes of the present invention involve separating the ethanol and ethyl acetate under low pressure conditions in a distillation column, referred to herein as a light-ends column. In one embodiment, the light-ends column operates at subatmospheric pressures ranging from 0.1 kPa to 100 kPa, e.g., from 0.1 kPa to 50 kPa or from 0.1 kPa to 35 kPa. In some embodiments, the light-ends column may operate at or near vacuum conditions. At these reduced pressures, the difference between the relative volatilities of ethanol and ethyl acetate advantageously increases allowing for a more efficient separation of these components.

In preferred embodiments of the invention, the crude ethanol product is fed to a first distillation column that separates the crude ethanol product into a first distillate and a first residue. The first distillate comprises ethanol, ethyl acetate, and other organics, and the first residue comprises unreacted acetic acid, and optionally water. Optionally, water may also be present in the first distillate, and may be removed using one or more adsorption units or membranes.

The first distillate is fed to a light-ends column that is operating under low pressure conditions. The light-ends column yields a second distillate comprising ethyl acetate and less than 30 wt. % ethanol, e.g., from 0.5 to 30 wt. %, and a second residue comprising 75 wt. % to 99.5 wt. % ethanol and less than 100 wppm ethyl acetate. The second distillate may also comprise acetaldehyde. In some embodiments, the second distillate may be recycled to the hydrogenation reactor. The process of the present invention advantageously provides an ethanol product from the second residue that requires minimal treatment to remove water and other organics. Optionally, an extractive agent, preferably comprising water, is fed to the light-ends column to facilitate removal of ethanol in the second residue.

In one preferred embodiment, the total amount of water fed to the light-ends column, including water from the first distillate as well as water in the extractive agent (if any), is less than 10 wt. %, e.g., less than 6 wt. % or less than 4 wt. %, based on the total weight of all components fed to the light-ends column. In terms of ranges, the total amount of water fed to the light-ends column preferably is from 1 to 10 wt. %, and more preferably from 2 to 6 wt. %. The addition of some water to the light-ends column may reduce the energy requirements for operating the light-ends column. For example, operating the light-ends column under low pressure conditions may reduce the energy requirements per ton of ethanol by at least 35%, e.g., at least 40% or at least 50%, relative to the same column operated at atmospheric pressure. However, as more water is fed to the light-ends column, the water concentration of the second residue increases requiring further treatment of the second residue to obtain a desired ethanol product. The amount of water in the final ethanol product may vary depending on the intended application. Additional water removal steps may be employed in the processes of the invention, for example, if an anhydrous ethanol product is desired.

Hydrogenation of Acetic Acid

The process of the present invention may be used with any hydrogenation process for producing ethanol. The materials, catalysts, reaction conditions, and separation processes that may be used in the hydrogenation of acetic acid are described further below.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum,* and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolyzed with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

The acetic acid fed to the hydrogenation reaction may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

Some embodiments of the process of hydrogenating acetic acid to form ethanol may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, or from 100 kPa to 1500 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

The hydrogenation of acetic acid to form ethanol is preferably conducted in the presence of a hydrogenation catalyst. Suitable hydrogenation catalysts include catalysts comprising a first metal and optionally one or more of a second metal, a third metal or any number of additional metals, optionally on a catalyst support. The first and optional second and third metals may be selected from Group IB, IIB, IIIB, IVB, VB, VIIB, VIIB, VIII transition metals, a lanthanide metal, an actinide metal or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, and ruthenium/iron. Exemplary catalysts are further described in U.S. Pat. No. 7,608,744 and U.S. Pub. No. 2010/0029995, the entireties of which are incorporated herein by reference. In another embodiment, the catalyst comprises a Co/Mo/S catalyst of the type described in U.S. Pub. No. 2009/0069609, the entirety of which is incorporated herein by reference.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. In embodiments of the invention where the first metal comprises platinum, it is preferred that the catalyst comprises platinum in an amount less than 5 wt. %, e.g., less than 3 wt. % or less than 1 wt. %, due to the high commercial demand for platinum.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from tin and rhenium.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 5 wt. %. For catalysts comprising two or more metals, the two or more metals may be alloyed with one another or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal preferably is from 0.05 to 4 wt. %, e.g., from 0.1 to 3 wt. %, or from 0.1 to 2 wt. %.

In addition to one or more metals, in some embodiments of the present invention the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 97 wt. %, or from 80 to 95 wt. %. In preferred embodiments that utilize a modified support, the support modifier is present in an amount from 0.1 to 50 wt. %, e.g., from 0.2 to 25 wt. %, from 0.5 to 15 wt. %, or from 1 to 8 wt. %, based on the total weight of the catalyst. The metals of the catalysts may be dispersed throughout the support, layered throughout the support, coated on the outer surface of the support (i.e., egg shell), or decorated on the surface of the support.

As will be appreciated by those of ordinary skill in the art, support materials are selected such that the catalyst system is suitably active, selective and robust under the process conditions employed for the formation of ethanol.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

As indicated, the catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $Co_2O_3$, and $Bi_2O_3$.

In another embodiment, the support modifier may be a basic modifier that has a low volatility or no volatility. Such basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). If the basic support modifier comprises calcium metasilicate, it is preferred that at least a portion of the calcium metasilicate is in crystalline form.

A preferred silica support material is SS61138 High Surface Area (HSA) Silica Catalyst Carrier from Saint Gobain NorPro. The Saint-Gobain NorPro SS61138 silica exhibits the following properties: contains approximately 95 wt. % high surface area silica; surface area of about 250 $m^2/g$; median pore diameter of about 12 nm; average pore volume of about 1.0 cm³/g as measured by mercury intrusion porosimetry and a packing density of about 0.352 g/cm³ (22 lb/ft³).

A preferred silica/alumina support material is KA-160 silica spheres from Sud Chemie having a nominal diameter of about 5 mm, a density of about 0.562 g/ml, an absorptivity of about 0.583 g H₂O/g support, a surface area of about 160 to 175 m²/g, and a pore volume of about 0.68 ml/g.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197485 referred to above, the entireties of which are incorporated herein by reference.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a mole percentage based on acetic acid in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 1 ton of ethanol per hour, e.g., at least 15 tons of ethanol per hour or at least 30 tons of ethanol per hour. In terms of ranges, for large scale industrial production of ethanol, the process of the present invention may produce from 0.1 to 160 tons of ethanol per hour, e.g., from 15 to 160 tons of ethanol per hour or from 30 to 80 tons of ethanol per hour. Ethanol production from fermentation, due the economies of scale, typically does not permit the single facility ethanol production that may be achievable by employing embodiments of the present invention.

In various embodiments of the present invention, the crude ethanol product produced by the hydrogenation process, before any subsequent processing, such as purification and separation, will typically comprise unreacted acetic acid, ethanol and water. As used herein, the term "crude ethanol product" refers to any composition comprising from 5 to 70 wt. % ethanol and from 5 to 40 wt. % water. Exemplary compositional ranges for the crude ethanol product are provided in Table 1. The "others" identified in Table 1 may include, for example, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 70 | 15 to 70 | 15 to 50 | 25 to 50 |
| Acetic Acid | 0 to 90 | 0 to 50 | 15 to 70 | 20 to 70 |
| Water | 5 to 40 | 5 to 30 | 10 to 30 | 10 to 26 |
| Ethyl Acetate | 0 to 30 | 0 to 20 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product may comprise acetic acid in an amount less than 20 wt. %, e.g., of less than 15 wt. %, less than 10 wt. % or less than 5 wt. %. In embodiments having lower amounts of acetic acid, the conversion of acetic acid is preferably greater than 75%, e.g., greater than 85% or greater than 90%. In addition, the selectivity to ethanol may also be preferably high, and is greater than 75%, e.g., greater than 85% or greater than 90%.

Ethanol Recovery

Figure 1:
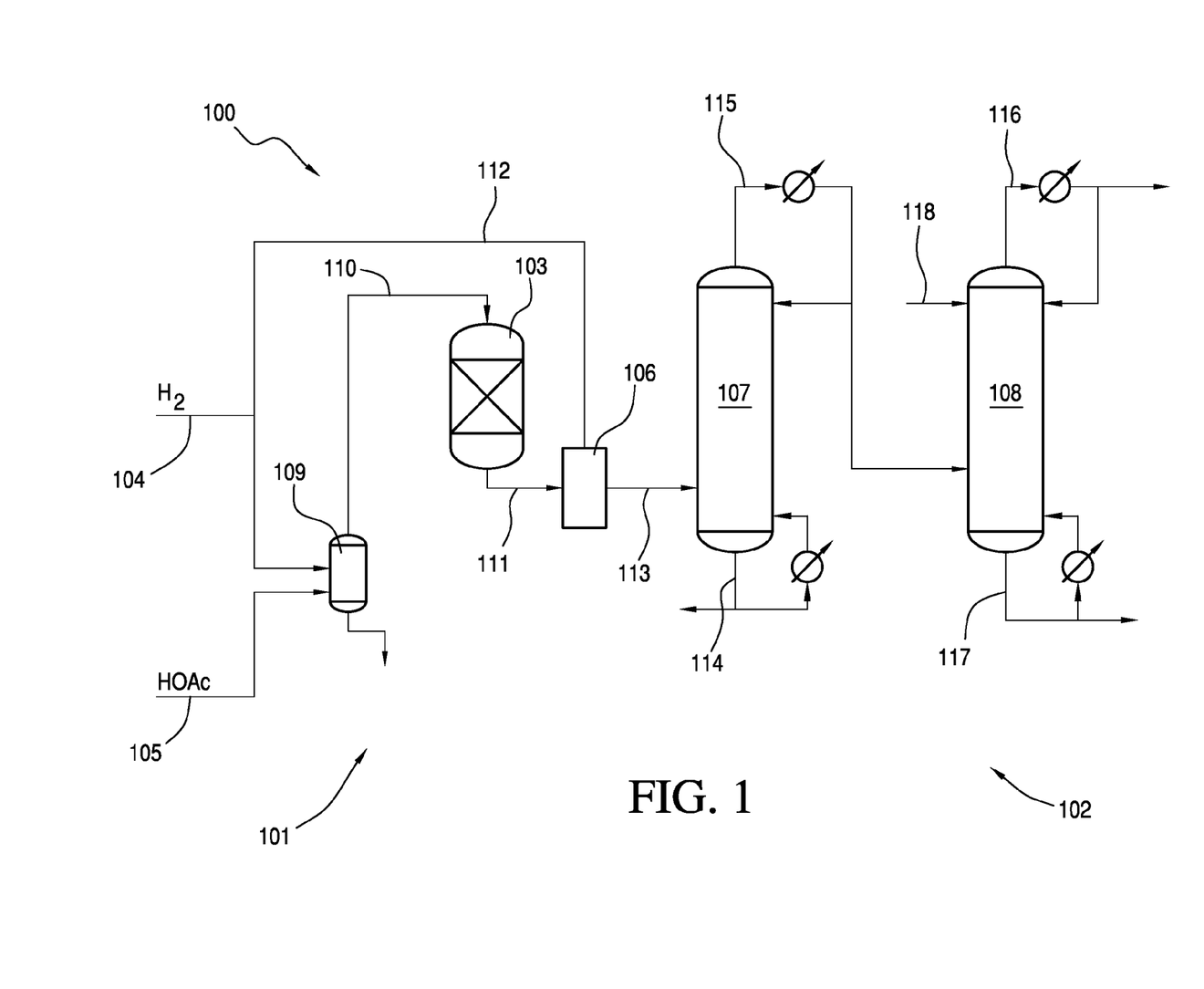
FIG. 1 is a schematic diagram of an ethanol production system using reduced pressure that yields a residue stream comprising ethanol and a distillate comprising ethyl acetate in accordance with one embodiment of the present invention.
Figure 2:
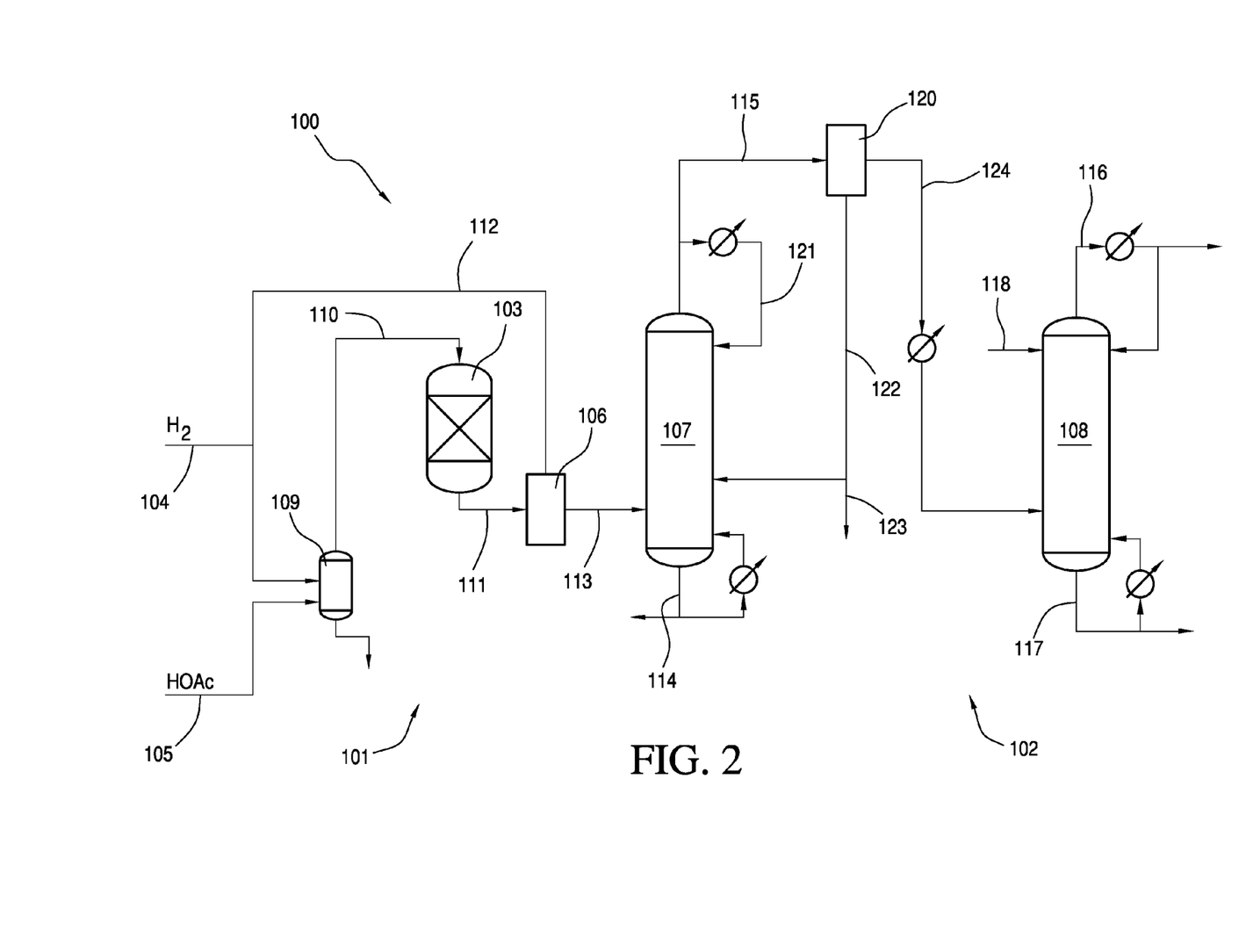
FIG. 2 is a schematic diagram of an ethanol production system for increasing the separation of ethanol and ethyl acetate in the light-ends column in accordance with one embodiment of the present invention.

Exemplary ethanol recovery systems in accordance with embodiments of the present invention are shown in FIGS. 1 and 2. Each hydrogenation system 100 provides a suitable hydrogenation reactor and a process for separating ethanol from the crude reaction mixture according to an embodiment of the invention. System 100 comprises reaction zone 101 and separation zone 102. Reaction zone 101 comprises reactor 103, hydrogen feed line 104 and acetic acid feed line 105. Separation zone 102 comprises a separator 106, a first distillation column 107, and a second distillation column 108. FIG. 2 also includes a water separator 120 for removing a portion of the water from the first distillate in line 115.

As shown in FIG. 1., hydrogen and acetic acid are fed to a vaporizer 109 via lines 104 and 105, respectively, to create a vapor feed stream in line 110 that is directed to reactor 103. In one embodiment, lines 104 and 105 may be combined and jointly fed to the vaporizer 109. The temperature of the vapor feed stream in line 110 is preferably from 100° C. to 350° C., e.g., from 120° C. to 310° C. or from 150° C. to 300° C. Any feed that is not vaporized is removed from vaporizer 109 and may be recycled or discarded thereto. In addition, although line 110 is shown as being directed to the top of reactor 103, line 110 may be directed to the side, upper portion, or bottom of reactor 103.

Reactor 103 contains the catalyst that is used in the hydrogenation of the carboxylic acid, preferably acetic acid. In one embodiment, one or more guard beds (not shown) may be used upstream of the reactor, optionally upstream of the vaporizer 109, to protect the catalyst from poisons or undesirable impurities contained in the feed or return/recycle streams. Such guard beds may be employed in the vapor or liquid streams. Suitable guard bed materials may include, for example, carbon, silica, alumina, ceramic, or resins. In one aspect, the guard bed media is functionalized, e.g., silver functionalized, to trap particular species such as sulfur or halogens. During the hydrogenation process, a crude ethanol product stream is withdrawn, preferably continuously, from reactor 103 via line 111.

The crude ethanol product stream in line 111 may be condensed and fed to a separator 106, which, in turn, provides a vapor stream 112 and a liquid stream 113. In some embodiments, separator 106 may comprise a flasher or a knockout pot. The separator 106 may operate at a temperature of from 20° C. to 250° C., e.g., from 30° C. to 225° C. or from 60° C. to 200° C. The pressure of separator 106 may be from 50 kPa to 2000 kPa, e.g., from 75 kPa to 1500 kPa or from 100 kPa to 1000 kPa. Optionally, the crude ethanol product in line 111 may pass through one or more membranes to separate hydrogen and/or other non-condensable gases.

The vapor stream 112 exiting separator 106 may comprise hydrogen and hydrocarbons, and may be purged and/or returned to reaction zone 101. As shown, vapor stream 112 is combined with the hydrogen feed 104 and co-fed to vaporizer 109. In some embodiments, the returned vapor stream 112 may be compressed before being combined with hydrogen feed 104.

The liquid stream 113 from separator 106 is withdrawn and pumped to the side of first column 107, also referred to as an "acid separation column" In one embodiment, the contents of liquid stream 113 are substantially similar to the crude ethanol product obtained from the reactor, except that the composition has been depleted of hydrogen, carbon dioxide, methane and/or ethane, which are removed by separator 106. Accordingly, liquid stream 113 may also be referred to as a crude ethanol product. Exemplary components of liquid stream 113 are provided in Table 2. It should be understood that liquid stream 113 may contain other components, not listed in Table 2.

TABLE 2

COLUMN FEED COMPOSITION
(Liquid Stream 113)

| | Conc. (wt. %) | Conc. (wt. %) | Conc. (wt. %) |
|---|---|---|---|
| Ethanol | 5 to 70 | 10 to 60 | 15 to 50 |
| Acetic Acid | <90 | 5 to 80 | 15 to 70 |
| Water | 5 to 40 | 5 to 30 | 10 to 30 |
| Ethyl Acetate | <30 | 0.001 to 20 | 1 to 12 |
| Acetaldehyde | <10 | 0.001 to 3 | 0.1 to 3 |
| Acetal | <5 | 0.001 to 2 | 0.005 to 1 |
| Acetone | <5 | 0.0005 to 0.05 | 0.001 to 0.03 |
| Other Esters | <5 | <0.005 | <0.001 |
| Other Ethers | <5 | <0.005 | <0.001 |
| Other Alcohols | <5 | <0.005 | <0.001 |

The amounts indicated as less than (<) in the tables throughout present specification are preferably not present and if present may be present in trace amounts or in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. The "other alcohols" in Table 2 may include, but are not limited to, methanol, isopropanol, n-propanol, n-butanol or mixtures thereof. In one embodiment, the liquid stream 113 may comprise propanol, e.g., isopropanol and/or n-propanol, in an amount from 0.001 to 0.1 wt. %, from 0.001 to 0.05 wt. % or from 0.001 to 0.03 wt. %. In should be understood that these other components may be carried through in any of the distillate or residue streams described herein and will not be further described herein, unless indicated otherwise.

Optionally, crude ethanol product in line 111 or in liquid stream 113 may be further fed to an esterification reactor, hydrogenolysis reactor, or combination thereof. An esterification reactor may be used to consume residual acetic acid present in the crude ethanol product to further reduce the amount of acetic acid that would otherwise need to be removed. Hydrogenolysis may be used to convert ethyl acetate in the crude ethanol product to ethanol.

Liquid stream 113 is introduced in the middle or lower portion of first column 107. In one embodiment, no entrainers are added to first column 107. In first column 107, water and unreacted acetic acid, along with any other heavy components, if present, are removed from liquid stream 113 and are withdrawn, preferably continuously, as a first residue in line 114. First column 107 also forms a first distillate, which is withdrawn in line 115, and which may be condensed and refluxed, for example, at a ratio of from 10:1 to 1:10, e.g., from 3:1 to 1:3 or from 1:2 to 2:1.

When first column 107 is operated under about 170 kPa, the temperature of the residue exiting in line 114 preferably is from 90° C. to 130° C., e.g., from 95° C. to 120° C. or from 100° C. to 115° C. The base of first column 107 may be maintained at a relatively low temperature by withdrawing a first residue stream comprising both water and acetic acid, thereby providing an energy efficiency advantage. The temperature of the first distillate exiting in line 115 preferably is from 60° C. to 90° C., e.g., from 65° C. to 85° C. or from 70° C. to 80° C. In some embodiments, the pressure of first column 107 may range from 0.1 kPa to 510 kPa, e.g., from 1 kPa to 475 kPa or from 1 kPa to 375 kPa. Exemplary components of the first distillate and first residue compositions for first column 107 are provided in Table 3 below. It should also be understood that the first distillate and first residue may also contain other components, not listed, such as components derived from the feed. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

| FIRST COLUMN 107 | | | |
|---|---|---|---|
| | Conc. (wt. %) | Conc. (wt. %) | Conc. (wt. %) |
| Distillate | | | |
| Ethanol | 20 to 90 | 30 to 85 | 50 to 85 |
| Water | 4 to 38 | 5 to 35 | 7 to 25 |
| Acetic Acid | <1 | 0.001 to 1 | 0.01 to 0.5 |

TABLE 3-continued

| FIRST COLUMN 107 | | | |
|---|---|---|---|
| | Conc. (wt. %) | Conc. (wt. %) | Conc. (wt. %) |
| Ethyl Acetate | 5 to 60 | 5 to 40 | 8 to 45 |
| Acetaldehyde | <10 | 0.001 to 5 | 0.01 to 4 |
| Acetal | <4.0 | <3.0 | <2.0 |
| Acetone | <0.05 | 0.001 to 0.03 | 0.01 to 0.025 |
| Residue | | | |
| Acetic Acid | <90 | 1 to 50 | 3 to 40 |
| Water | 30 to 100 | 45 to 90 | 60 to 90 |
| Ethanol | <1 | <0.9 | <0.5 |

In one embodiment, the water concentration of the first distillate in 115 may be less than 10 wt. %, e.g., from 1 to 10 wt % or from 2 to 6 wt. %. When the water concentration in the first distillate in line 115 is greater than 10 wt. %, it is preferred to remove a portion of the water using a water separator 120 as discussed below with reference to FIG. 2.

In another embodiment, under high conversion conditions, e.g., greater than 90% acetic acid conversion or greater than 99% acetic acid conversion, it may be advantageous to withdraw a first residue in line 114 that primarily comprises water. The minor amounts of acetic acid, if any, may be withdrawn with the water in the bottom of the first column 107.

Some species, such as acetals, may decompose in column 107 such that very low amounts, or even no detectable amounts, of acetals remain in the distillate or residue. In addition, an equilibrium reaction between acetic acid and ethanol or between ethyl acetate and water may occur in the crude ethanol product after it exits reactor 103. Depending on the concentration of acetic acid in the crude ethanol product, this equilibrium may be driven toward formation of ethyl acetate. This reaction may be regulated using the residence time and/or temperature of crude ethanol product.

The first distillate in line 115 preferably comprises ethanol, ethyl acetate, acetaldehyde and optionally water. Preferably, the first distillate in line 115 is substantially free of acetic acid and may contain, if any, only trace amounts of acetic acid. In FIG. 1, the first distillate in line 115 is introduced to a second column 108, also referred to as the "light ends column," to remove ethyl acetate and acetaldehyde from the first distillate in line 115. Ethyl acetate is removed in a second distillate in line 116 and ethanol is removed as the second residue in line 117. Second column 108 may be a tray column or packed column. In one embodiment, second column 108 is a tray column having from 5 to 70 trays, e.g., from 15 to 50 trays or from 20 to 45 trays.

As indicated above, second column 108 preferably operates at subatmospheric pressures ranging from 0.1 kPa to 100 kPa, e.g., from 0.1 kPa to 50 kPa or from 0.1 kPa to 35 kPa. Although the temperature of second column 108 may vary, when at about 20 kPa to 70 kPa, the temperature of the second residue exiting in line 117 preferably is from 30° C. to 75° C., e.g., from 35° C. to 70° C. or from 40° C. to 65° C. The temperature of the second distillate exiting in line 116 preferably is from 20° C. to 55° C., e.g., from 25° C. to 50° C. or from 30° C. to 45° C.

The total concentration of water fed to second column 108 preferably is less than 10 wt. %, as discussed above. When first distillate in line 115 comprises minor amounts of water, e.g., less than 1 wt. % or less than 0.5 wt. %, additional water may be fed to second column 108 as an extractive agent in line 118. Line 118 may be introduced to second column 108 above the feed point of the first distillate in line 115. A sufficient amount of water is preferably added via the extractive agent in line 118 such that the total concentration of water fed to second column 108 is from 1 to 10 wt. % water, e.g., from 2 to 6 wt. %, based on the total weight of all components fed to second column 108. If the extractive agent comprises water, the water may be obtained from an external source or from an internal return/recycle line from one or more of the other columns or water separators.

Suitable extractive agents may also include, for example, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N'-dimethyl-1,3-propanediamine, N,N'-dimethylethylenediamine, diethylene triamine, hexamethylene diamine and 1,3-diaminopentane, an alkylated thiopene, dodecane, tridecane, tetradecane, chlorinated paraffins, or a combination thereof. When extractive agents are used, a suitable recovery system, such as a further distillation column, may be used to remove the extractive agent and recycle the extractive agent.

Exemplary components for the second distillate and second residue compositions for the second column 108 are provided in Table 4, below. It should be understood that the distillate and residue may also contain other components, not listed in Table 4.

TABLE 4

| SECOND COLUMN 108 | | | |
|---|---|---|---|
| | Conc. (wt. %) | Conc. (wt. %) | Conc. (wt. %) |
| Second Distillate | | | |
| Ethyl Acetate | 10 to 90 | 25 to 90 | 50 to 90 |
| Acetaldehyde | 1 to 25 | 1 to 15 | 1 to 8 |
| Water | 1 to 10 | 1 to 7 | 1 to 16 |
| Ethanol | <30 | 0.001 to 15 | 0.01 to 11 |
| Acetal | <5 | 0.001 to 2 | 0.01 to 1 |
| Second Residue | | | |
| Ethanol | 75 to 99.5 | 80 to 96 | 85 to 96 |
| Water | <12 | 1 to 9 | 3 to 8 |
| Ethyl Acetate | <0.01 | <0.005 | <0.001 |
| Acetic Acid | <1 | 0.001 to 0.1 | 0.005 to 0.01 |

The final ethanol product produced by the process of the present invention may be taken from the second residue in line 117. Any of the compounds that are carried through the separation process from the feed or crude reaction product generally remain in the ethanol residue in an amount less than 0.1 wt. %, based on the total weight of the second residue, e.g., less than 0.05 wt. % or less than 0.02 wt. %.

The second distillate in line 116, which comprises ethyl acetate and/or acetaldehyde, preferably is refluxed as shown in FIG. 1, for example, at a reflux ratio of from 1:30 to 30:1, e.g., from 1:10 to 10:1 or from 1:3 to 3:1. In one aspect, not shown, the second distillate 116 or a portion thereof may be returned to reactor 103. In some embodiments, it may be advantageous to return a portion of second distillate to reactor 103. The ethyl acetate and/or acetaldehyde in the second distillate may be further reacted in hydrogenation reactor 103 or in a secondary reactor. The outflow from the secondary reactor may be fed to reactor 103 to produce additional ethanol or to any of the distillation columns to recover additional ethanol.

In one embodiment, the second distillate in line 116 and/or a refined second distillate, or a portion of either or both streams, may be further separated to produce an acetaldehyde-containing stream and an ethyl acetate-containing stream. This may allow a portion of either the resulting acetaldehyde-containing stream or ethyl acetate-containing stream to be recycled to reactor 103 while purging the other stream. The purge stream may be valuable as a source of either ethyl acetate and/or acetaldehyde.

In another embodiment of the invention, water may be removed from the first distillate in line 115 as shown in FIG. 2. In this aspect, a portion of first distillate in line 115 may be condensed and refluxed via line 121, for example, at a ratio of 10:1 to 1:10, e.g., 3:1 to 1:3 or 2:1 to 1:2. The remaining portion of the first distillate in line 115 is fed, preferably in the vapor phase, to a water separator 120. Water separator 120 may comprise one or more adsorption units, membranes, extractive column distillations, or a combination thereof. Suitable adsorption units include pressure swing adsorption (PSA) units and thermal swing adsorption (TSA) units.

A membrane or an array of membranes may also be employed to separate water from the distillate. The membrane or array of membranes may be selected from any suitable membrane that is capable of removing a permeate water stream from a stream that also comprises ethanol and ethyl acetate.

In a preferred embodiment, water separator 120 is a pressure swing adsorption (PSA) unit. The PSA unit is optionally operated at a temperature from 30° C. to 160° C., e.g., from 80° C. to 140° C., and a pressure of from 0.01 kPa to 550 kPa, e.g., from 1 kPa to 150 kPa. The PSA unit may comprise from two to five beds. Water separator 120 may remove at least 95% of the water from the first distillate in line 115, and more preferably from 99% to 99.99% of the water from the first distillate, in a water stream 122. All or a portion of water stream 122 may be returned to first column 107, where it preferably is ultimately recovered from first column 107 in first residue 114. Additionally or alternatively, all or a portion of water stream 122 may be purged via line 123. The remaining portion of first distillate 115 exits the water separator 120 as ethanol mixture stream 124.

Ethanol mixture stream 124 comprises ethanol and ethyl acetate and is introduced to second column 108 as discussed above. Depending on the water concentration, a portion of the reflux line 121 or water stream 122 may be fed as the extractive agent in line 118 into second column 108. The water separator 120 shown in FIG. 2 allows control of the amount of water that is fed to second column 108, in particular when first distillate 115 comprises more than 10 wt. % water.

Depending on the amount of water and acetic acid contained in the residue of first column 107, first residue 114 may be treated in one or more of the following processes. The following are exemplary processes for further treating first residue and it should be understood that any of the following may be used regardless of acetic acid concentration. When the residue comprises a majority of acetic acid, e.g., greater than 70 wt. %, the residue may be recycled to the reactor without any separation of the water. In one embodiment, the residue may be separated into an acetic acid stream and a water stream when the residue comprises a majority of acetic acid, e.g., greater than 50 wt. %. Acetic acid may also be recovered in some embodiments from first residue having a lower acetic acid concentration. The residue may be separated into the acetic acid and water streams by a distillation column or one or more membranes. If a membrane or an array of membranes is employed to separate the acetic acid from the water, the membrane or array of membranes may be selected from any suitable acid resistant membrane that is capable of removing a permeate water stream. The resulting acetic acid stream optionally is returned to reactor 103. The resulting water stream may be used as an extractive agent or to hydrolyze an ester-containing stream in a hydrolysis unit.

In other embodiments, for example, where first residue 114 comprises less than 50 wt. % acetic acid, possible options include one or more of: (i) returning a portion of the residue to reactor 103, (ii) neutralizing the acetic acid, (iii) reacting the acetic acid with an alcohol, or (iv) disposing of the residue in a waste water treatment facility. It also may be possible to separate a residue comprising less than 50 wt. % acetic acid using a weak acid recovery distillation column to which a solvent (optionally acting as an azeotroping agent) may be added. Exemplary solvents that may be suitable for this purpose include ethyl acetate, propyl acetate, isopropyl acetate, butyl acetate, vinyl acetate, diisopropyl ether, carbon disulfide, tetrahydrofuran, isopropanol, ethanol, and $C_3$-$C_{12}$ alkanes. When neutralizing the acetic acid, it is preferred that the first residue 114 comprises less than 10 wt. % acetic acid. Acetic acid may be neutralized with any suitable alkali or alkaline earth metal base, such as sodium hydroxide or potassium hydroxide. When reacting acetic acid with an alcohol, it is preferred that the residue comprises less than 50 wt. % acetic acid. The alcohol may be any suitable alcohol, such as methanol, ethanol, propanol, butanol, or mixtures thereof. The reaction forms an ester that may be integrated with other systems, such as carbonylation production or an ester production process. Preferably, the alcohol comprises ethanol and the resulting ester comprises ethyl acetate. Optionally, the resulting ester may be fed to the hydrogenation reactor.

In some embodiments, when the residue comprises very minor amounts of acetic acid, e.g., less than 5 wt. %, the residue may be disposed of to a waste water treatment facility without further processing. The organic content, e.g., acetic acid content, of the residue beneficially may be suitable to feed microorganisms used in a waste water treatment facility.

The columns shown in FIGS. 1-2 may comprise any distillation column capable of performing the desired separation and/or purification. Each column preferably comprises a tray column having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The associated condensers and liquid separation vessels that may be employed with each of the distillation columns may be of any conventional design and are simplified in the figures. Heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and one flasher are shown in the figures, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in the columns may vary. As a practical matter, pressures from 10 kPa to 3000 kPa will generally be employed in these zones although in some embodiments subatmospheric pressures or superatmospheric pressures may be employed. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

The final ethanol product produced by the processes of the present invention may be taken from the second residue 117. The ethanol product may be an industrial grade ethanol comprising from 75 to 96 wt. % ethanol, e.g., from 80 to 96 wt. % or from 85 to 96 wt. % ethanol, based on the total weight of the ethanol product. Exemplary finished ethanol compositional ranges are provided below in Table 5.

TABLE 5

FINISHED ETHANOL COMPOSITIONS

| Component | Conc. (wt. %) | Conc. (wt. %) | Conc. (wt. %) |
|---|---|---|---|
| Ethanol | 75 to 96 | 80 to 96 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm.

In some embodiments, when further water separation is used, the ethanol product may be withdrawn as a stream from the water separation unit as discussed above. In such embodiments, the ethanol concentration of the ethanol product may be greater than indicated in Table 5, and preferably is greater than 97 wt. % ethanol, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including applications as fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

In order that the invention disclosed herein may be more efficiently understood, an example is provided below. It should be understood that these examples are for illustrative purposes only and is not to be construed as limiting the invention in any manner.

EXAMPLE 1

The following examples were prepared with ASPEN Plus 7.1 simulation software to test various feed composition and separation systems.

A crude ethanol product was separated in a first column into a first distillate and a first residue. The first distillate was sent to a second column, which formed a second distillate and a second residue. Table 6 shows the composition of each stream. Run A was run at atmospheric pressure and demonstrated significant amounts of ethanol in the second distillate. Run B was run at a pressure of 34.7 kPa and included a water separator as shown in FIG. 2 to remove water from the first distillate.

TABLE 6

| | A | | | B | | |
|---|---|---|---|---|---|---|
| | EtOH | EtOAc | $H_2O$ | EtOH | EtOAc | $H_2O$ |
| First Distillate (wt. %) | 57.6 | 15.1 | 24.7 | 74.2 | 12.2 | 11.7 |
| First Distillate After Water Separation (wt. %) | — | — | — | 84.1 | 13.9 | 0 |
| Second Distillate (wt. %) | 12.4 | 76.0 | 5.1 | 34.2 | 61.7 | 0 |
| Second Residue (wt. %) | 67.6 | nd | 30.8 | 98.7 | 0 | 1.3 |
| Pressure in Second Column | 101 kPa | | | 34.7 kPa | | |

EXAMPLE 2

Figure 3:
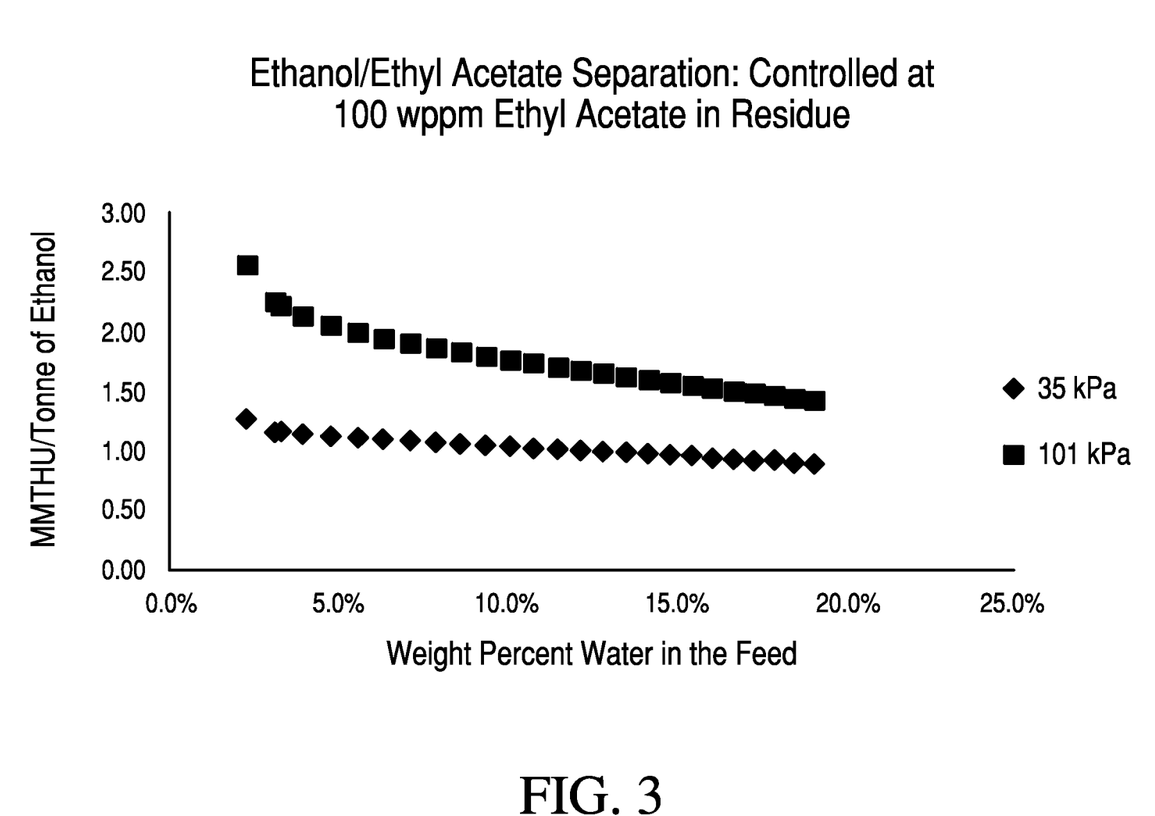
FIG. 3 is a graph showing the weight percent of water in the feed versus the amount of energy required for the ethanol/ethyl acetate separation in the second distillation column.

A first distillate comprising ethanol and ethyl acetate from a first column was introduced to a second column. The light ends column, e.g., second column, was operated at a pressure of about 35 kPa. The second residue was controlled to maintain an ethyl acetate concentration of less than 100 wppm. By varying the water concentration that was fed to the column, an energy reduction was realized as shown in FIG. 3. A comparison was conducted by feeding a first distillate with the same composition through a second column that operated at a pressure of about 101 kPa. As shown in FIG. 3, less energy was required to separate ethanol and ethyl acetate when the second column was run at reduced pressure, i.e. 35 kPa. FIG. 3 also shows that the increase in water percentage in the feed did not increase the amount of energy required to separate ethanol and ethyl acetate. Further separation of water from the second residue may be accomplished by using an adsorption unit (PSA or TSA) or membrane.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing ethanol, comprising the steps of:
   hydrogenating acetic acid from an acetic acid feed stream in a reactor to form a crude ethanol product comprising ethanol, ethyl acetate, water, and acetic acid;
   separating at least a portion of the crude ethanol product in a first column into a first distillate comprising ethanol and ethyl acetate and a first residue comprising water and acetic acid; and
   separating at least a portion of the first distillate in a second column into a second distillate comprising ethyl acetate and less than 30 wt. % ethanol and a second residue comprising ethanol and less than 100 wppm ethyl acetate, wherein a total concentration of water fed to the second column is less than 10 wt. %, based on the total weight of all components fed to the second column and wherein the second distillation column operates from 0.1 to 100 kPa.

2. The process of claim 1, wherein the total concentration of water fed to the second column is from 2 to 6 wt. %.

3. The process of claim 1, wherein an extractive agent comprising water is fed to the second column.

4. The process of claim 1, wherein the first distillate comprises less than 10 wt. % water.

5. The process of claim 1, wherein water is removed from the first distillate using an adsorption unit, membrane, extractive column distillation, or a combination thereof, to yield an ethanol mixture stream comprising less than 10 wt. % water.

6. The process of claim 1, wherein the second distillation column operates from 0.1 to 35 kPa.

7. A process for producing ethanol, comprising the steps of:
   hydrogenating acetic acid from an acetic acid feed stream in a reactor to form a crude ethanol product comprising ethanol, ethyl acetate, and water;
   separating at least a portion of the crude ethanol product in a first column into a first distillate comprising ethanol and ethyl acetate and a first residue comprising water; and
   separating at least a portion of the first distillate in a second column operating at a pressure from 0.1 to 100 kPa into a second distillate comprising ethyl acetate and less than 30 wt. % ethanol and a second residue comprising ethanol and less than 100 wppm ethyl acetate, wherein a total concentration of water fed to the second column is less than 10 wt. %, based on the total weight of all components fed to the second column.

8. The process of claim 7, wherein the second distillation column operates from 0.1 to 35 kPa.

9. The process of claim 7, wherein the acetic acid conversion in the reactor is greater than 90%.

10. The process of claim 7, wherein the total concentration of water fed to the second column is from 2 to 6 wt. %.

11. The process of claim 7, wherein the second residue comprises less than 50 wppm ethyl acetate.

12. The process of claim 7, wherein water is removed from the first distillate using an adsorption unit, membrane, extractive column distillation, or a combination thereof, to yield an ethanol mixture stream comprising less than 10 wt. % water.

13. The process of claim 7, wherein the acetic acid is formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

14. The process of claim 1, wherein the acetic acid is formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

15. The process of claim 1, wherein the acetic acid conversion in the reactor is greater than 90%.

16. The process of claim 1, wherein the second residue comprises less than 50 wppm ethyl acetate.

* * * * *